United States Patent [19]

Klosa

[11] 4,189,487
[45] Feb. 19, 1980

[54] USE OF PYRIDINE ALDEHYDES FOR THE PREVENTION AND TREATMENT OF ACNE VULGARIS

[76] Inventor: Josef Klosa, Janickestrasse 13, 1000 Berlin 37-Zehlendorf, Fed. Rep. of Germany

[21] Appl. No.: 886,820

[22] Filed: Mar. 15, 1978

[30] Foreign Application Priority Data

Mar. 17, 1977 [DE] Fed. Rep. of Germany ....... 2712078
Nov. 22, 1977 [DE] Fed. Rep. of Germany ....... 2752134

[51] Int. Cl.$^2$ .............................................. A61K 31/44
[52] U.S. Cl. .................................................... 424/263
[58] Field of Search ......................................... 424/263

[56] References Cited

U.S. PATENT DOCUMENTS

| 3,482,923 | 12/1969 | Boosen et al. | ........................ 8/10 X |
| 3,960,932 | 6/1976 | Heck | ................. 260/479 R |
| 4,021,572 | 5/1977 | Van Scott et al. | .................. 424/317 |

OTHER PUBLICATIONS

Handbook of Non-Prescription Drugs, Fifth Ed. (1977) pp. 317-318.
Merck Index (1960) 7th Ed. p. 137.

*Primary Examiner*—Allen J. Robinson
*Attorney, Agent, or Firm*—Birch, Stewart, Kolasch and Birch

[57] ABSTRACT

A therapeutic composition for the treatment of acne vulgaris comprising a pyridine aldehyde compound of the formula:

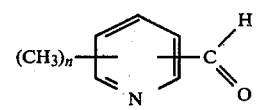

wherein n is 0 or 1. Also the process for the treatment of acne vulgaris comprising applying said pyridine aldehyde to the lesions thereof.

6 Claims, No Drawings

USE OF PYRIDINE ALDEHYDES FOR THE PREVENTION AND TREATMENT OF ACNE VULGARIS

BACKGROUND AND SUMMARY OF THE INVENTION

Acne vulgaris is a multifactorial disease with a seborrhoeic basis. Acne tends to appear during puberty and tends to fade away again, usually spontaneously when growth has stopped. Only rarely does it die away before the age of 20, and occasionally it is still to be found at the age of about 30. Since the face is one of the favorite locations affected and in severe cases the alterations give rise to considerable disfigurement, they have great aesthetic significance and they make it easy to comprehend the physical burden of the afflicted person.

Seborrhoea is a prerequisite for acne vulgaris. However, seborrhoea is certainly not the sole factor. In addition, there has to be a tendency toward the formation of follicular hyperkeratosis and, therefore, toward comedones. These formations, which are also called blackheads, represent plugs which close the excretory ducts of the sebaceous glands, i.e., the upper follicle excretory ducts, and mark the follicle ostia as dark spots.

The main foci of acne are the areas with an abundance of sebaceous glands, i.e., face, chest, neck and back.

For treating acne it is recommended to carry out a hot wash with Syndets. Following this a localized treatment is effected with, for example, sulphur, resorcinol, salicyclic acid, benzoyl peroxide or vitamin A acids.

All the known preparations have one or more disadvantages, e.g., lack of effectiveness. Accordingly, the cure rate with vitamin A acids is between 25 and 30%. This low success rate is due not only to the low stability of vitamin A acids but also to undesirable and distressing side effects.

The U.S. Pat. No. 4,021,572 discloses the use of lactic acid amides and quaternary ammonium lactates for the prevention and treatment of acne vulgaris.

The Belgian Patent Specification No. 753,823 discloses preparations for the localized treatment of acne vulgaris and seborrhoea, which contain a thio-ether of a 2-methyl-3-hydroxy-4-hydroxy-methylpyridine having the general formula:

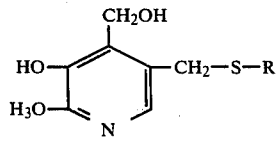

where R signifies an organic radical containing at least one amino group and, optionally, one carboxyl group. The carboxyl group may be esterified or amidated, whereas the amino group is present either in the form of a salt of an inorganic or organic acid, or may be substituted by an acyl group or sulphonyl group or one or two optionally substituted alkyl radicals.

Finally, the French Patent Specification No. 2,308,354 relates to a preparation for the localized treatment of acne and containing benzaldehyde as the active substance.

After exhaustive research into the pharmacological properties of pyridine aldehydes, it has surprisingly been found that pyridine aldehydes, particularly pyridine-3-aldehyde, in concentrations of from 0.05 to 5% by weight, preferably 0.1 to 3% by weight, can cure acne vulgaris within a short time and can also improve the appearance of the skin as well as cleansing it thoroughly.

The invention is thus based on the object of making available preparations containing pyridine aldehydes, in particular pyridine-3-aldehyde, for the localized treatment of acne vulgaris. A further object of the invention is to develop a method for the localized treatment of acne vulgaris, in which a pyridine aldehyde, preferably a pyridine-3-aldehyde, is used as the active substance.

The expression 'localized treatment of acne vulgaris' means the prophylaxis and therapy of the skin of a person who is prone to acne vulgaris or who is suffering from acne vulgaris.

The pyridine aldehydes used according to the invention have the formula:

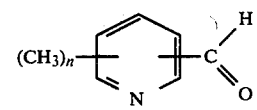

where n has the value 0 or 1. The aldehyde group is in the 2-, 3- or 4-position and the methyl group in the 2- or 6-position. Particular examples of pyridine aldehydes which can be used according to the invention are pyridine-2-aldehyde, pyridine-3-aldehyde, 2-methyl pyridine-3-aldehyde, 6-methyl pyridine-2-aldehyde and pyridine-4-aldehyde. Pyridine-3-aldehyde is particularly preferred. Accordingly, the invention will be described below with reference to this compound. These pyridine aldehydes are known and can be produced easily according to conventional processes.

The mechanism of the action of pyridine aldehydes in the invention and treatment of acne vulgaris is not yet known.

Suitable preparations, according to the invention, for the prevention and treatment of acne vulgaris are, for example, aqueous alcoholic solutions, and solutions in alcohols, polyglycols, lactic acid esters, phenylalkanols such as benzyl alcohol or phenyl ethanol or mixtures thereof. Special examples of alcohols which can be used are ethanol, propanol and propylene glycol. The preparations may contain additives, such as ethereal oils, azulene oils or conifer oils. Lactic acid ethyl ester may be incorporated into the liquid preparations as an antioxidant. It is preferable to add lactic acid ethyl ester in a quantity of from 5 to 40% by weight. The addition of glycerine or polyethylene glycol results in preparations which keep the skin moist and smooth. Ointments, creams, jellies and lotions may also incorporate the pyridine aldehydes, optionally together with preservatives, such a butylated hydroxy toluene or tocopherols.

According to the concentration of pyridine aldehyde, within the first few minutes after applying the preparations to the skin, reddening and warming of the skin region takes place. This effect lasts for approximately one hour. After several days of applying the solutions, jellies, lotions, creams or powders, the complexion of the normally markedly pallid juvenile acne sufferer becomes pleasantly ruddy and of healthy appearance. The preparations are applied two or three times a week to the skin so as to ensure the healing action.

Under the treatment with the pyridine aldehydes used according to the invention, within a few days, in persistent cases at latest after four to six weeks, the blackheads, pustules and pus-foci disappear. The skin is improved in appearance, the paleness diminishes and the large undesirable skin pores contract to normal size. Such an effect is not found in any of the known acne-treating agents.

The following examples illustrate the manufacture of acne preparations.

EXAMPLE 1

The following constituents are used to manufacture a solution:
pyridine-3-aldehyde: 0.5 ml
perfume oil: 1.0 ml
95% ethanol: up to 100.0 ml Method of manufacture:
The pyridine-3-aldehyde is first dissolved in 50 ml of ethanol, then 1 ml of perfume oil is added. After this it is made up to 100 ml with ethanol.

Instead of pyridine-3-aldehyde it is also possible to use pyridine-2-aldehyde, pyridine-4-aldehyde or 6-methylpyridine-2-aldehyde.

EXAMPLE 2

The following constituents are used to manufacture a solution according to Example 1:
pyridine-3-aldehyde: 1.0 ml
polyethylene glycol, mol. wt. 200: 50.0 ml
perfume oil: 2.0 ml
96% ethanol: up to 100.0 ml

EXAMPLE 3

The following constituents are used to produce a solution according to Example 1:
pyridine-3-aldehyde: 1.0 ml
benzyl alcohol: 10.0 ml
phenyl ethyl alcohol: 15.0 ml
polyethylene glycol, mol. wt. 200: 30.0 ml
perfume oil: 3.0 ml
96% ethanol: up to 100.0 ml

EXAMPLE 4

The following constituents are used to produce a solution according to Example 1:
pyridine-3-aldehyde: 0.5 ml
phenyl ethyl alcohol: 20.0 ml
benzyl alcohol: 10.0 ml
lactic acid ethyl ester: 30.0 ml
polyethylene glycol, mol. wt. 400: 20.0 ml
perfume oil: 2.0 ml
96% ethanol: up to 100.00 ml

EXAMPLE 5

The following constituents are used to produce a solution according to Example 1:
pyridine-3-aldehyde: 0.1 ml
lactic acid ethyl ester: 10.0 ml
96% ethanol: up to 100.0 ml

EXAMPLE 6

The following constituents are used to produce a fat based cream:

| | | |
|---|---|---|
| pyridine-3-aldehyde | 0.06 | parts by weight |
| cetyl alcohol | 3.00 | parts by weight |
| spermaceti | 10.00 | parts by weight |
| hydrogenated peanut oil | 86.40 | parts by weight |
| | 100.00 | |

Method of manufacture:
Spermaceti and hydrogenated peanut oil are melted under the action of heat. After cooling, pyridine-3-aldehyde is mixed in. A fat-based cream is obtained.

EXAMPLE 7

The following constituents are used to produce a jelly:
pyridine-3-aldehyde: 0.05 g
butylated hydroxy anisole: 0.10 g
hydroxypropyl cellulose: 5.00 g
propylene glycol: up to 100.00 g

EXAMPLE 8

The following constituents are thoroughly mixed together to produce a jelly:
pyridine-3-aldehyde: 1.00 g
α-tocopherol: 1.00 g
hydroxyethyl cellulose: 3.00 g
96% ethanol: up to 100.00 g

EXAMPLE 9

The following constituents are used to produce a jelly:
pyridine-3-aldehyde: 2.50 g
α-tocopherol: 0.50 g
acrylic acid polymer (Carbopol 940; thickener): 2.00 g
perfume oil: 1.00 g
isopropanol: up to 100.00 g Method of manufacture:
The α-tocopherol is dissolved in half the amount of isopropanol, then the acrylic acid polymer is added in small quantities and then pyridine-3-aldehyde is added. The mixture is agitated until it is completely solvated. After the addition of solution of a perfume oil in isopropanol a jelly is obtained.

EXAMPLE 10

A jelly is produced from the following constituents according to Example 9:
pyridine-3-aldehyde: 2.00 g
α-tocopherol: 1.00 g
hydrocortisone: 0.50 g
hydroxypropyl cellulose: 0.50 g
propylene glycol: 40.00 g
96% ethanol: up to 100.00 g

EXAMPLE 11

The following constituents are mixed together to form a solution:

| | |
|---|---|
| pyridine-3-aldehyde | 0.5 g |
| lactic acid ethyl ester | 20.0 g |
| benzyl alcohol | 10.0 g |
| phenyl ethyl alcohol | 15.0 g |
| polypropylene glycol, mol. wt. 200 | 27.0 g |
| 98% ethyl alcohol | 24.5 g |
| perfume oil | 3.0 g |
| | 100.00 g |

Method of manufacture:
3.0 g perfume oil is dissolved in 24.5 ml ethanol, then 0.5 g pyridine-3-aldehyde is mixed in and after that, one after the other, lactic acid ethyl ester, benzyl alcohol, phenyl ethyl alcohol and polypropylene glycol. The mixture is agitated for 10 minutes and a clear, fragrant solution is obtained.

As perfume oil there was used a stable and neutral preparation, No. 2908 of the firm Payan Bertrand, 06 Grasse, France.

Application of the preparation in dermatology:

(A) A 17 year old schoolboy who had been suffering from acne papulosa et pustulosa since his 13th year and who had previously been unsuccessfully treated with tetracycline and various acne treating agents, was treated twice daily, morning and evening, by dabbing the solution according to Example 1 onto his face. From the 2nd day the comedones started to disappear, and there took place retraction of the pustules, reduction of the severe inflammation of the acne accompanied by a sensation of tension in the skin and itchiness. From the 8th day the face was clear and free of pustules and blackheads.

Similar success was achieved with 10 other patients suffering from acne vulgaris, of both sexes and similar age. Perfume oil or ethanol alone or mixed together have no effect.

(B) A total of 23 patients of either sex and aged from 13 to 28 years participated in a further test. For unspecified reasons one of the patients dropped out after two weeks. Two other patients pulled out of the test after five weeks as a result of incompatibility.

The patients were directed to apply to their faces the acne solution according to Example 11, morning and evening, using the finger tips, in the region of the acne lesions. Cleansing of the face was to be carried out in the usual manner. An existing low-dosage, oral tetracycline treatment, which had been adopted by some patients for at least three months without noticeable success, was not interrupted. The same applied to contraceptives taken previously for a long time. Externally no additional substances were used during the treatment lasting eight weeks. Before treatment and after two, four, six and eight weeks, the individual efflorescences on the entire face were counted as the treatment continued.

The degree of inflammation of the active pimples and pustules was assessed by way of a classification scale of four crosses, in which one cross signified the lowest degree of inflammation and four crosses the severest degree of inflammation.

Additionally, the patient judged any improvement or deterioration in his skin condition by way of a scale which ranged from −10 to 0 (starting value) up to +10. By marking an entry the patient recorded his subjective impression on the corresponding line at each visit, without being shown his own assessment at the time of the last visit.

The following results were obtained.

| 1. | Open comedones, % | | | | |
|---|---|---|---|---|---|
| | 0W | 2W | 4W | 6W | 8W |
| | 100 | 67 | 56 | 57 | 40 |
| 2. | Closed comedones, % | | | | |
| | 0W | 2W | 4W | 6W | 8W |
| | 100 | 85 | 83 | 80 | 73 |
| 3. | Pustules, % | | | | |
| | 0W | 2W | 4W | 6W | 8W |
| | 100 | 52 | 32 | 14 | 22 |
| 4. | Active pimples, % | | | | |
| | 0W | 2W | 4W | 6W | 8W |
| | 100 | 79 | 61 | 59 | 57 |
| 5. | Subsiding pimples, % | | | | |
| | 0W | 2W | 4W | 6W | 8W |
| | 100 | 166 | 201 | 178 | 141 |
| 6. | Erythema patches, % | | | | |
| | 0W | 2W | 4W | 6W | 8W |
| | 100 | 139 | 146 | 140 | 134 |
| 7. | Degree of inflammation, % | | | | |
| | 0W | 2W | 4W | 6W | 8W |
| | 100 | 75 | 65 | 56 | 56 |
| 8. | Subjective assessment, % | | | | |
| | 0W | 2W | 4W | 6W | 8W |
| | 0 | +3.42 | +2.22 | +3.46 | +5.00 |

For the first examination (OW) and also for each subsequent visit there were calculated for the individual efflorescence counts and the degree of inflammation the average values of those patients who participated up to the end of the test (20 patients). The mean value obtained for OW was set at 100% and the other values calculated accordingly for the visits after two weeks, four weeks, six weeks and eight weeks.

The subjective assessment resulted from the mean values on the scale −10 to +10.

Results and Discussion

1. Open Comedones

Even after two weeks there is a reduction in the efflorescence counts (67%) which greatly exceeds that which may be regarded as a placebo effect (10%). After four weeks, a reduction to about one-half (56%) is achieved and at the end of the treatment period only 40% of the open comedones are still present which were counted at the start of the test.

2. Closed Comedones

In this case a slow but constant lessening of the efflorescences takes place down to 73% after eight weeks.

3. Pustules

Of all efflorescences the pustules show the greatest decrease. Even after two weeks only half as many are present as at the outset (52%), and after six weeks they reach their lowest level at 14%. At the end of the test, they are at 22%, almost just as low.

4. Active Pimples

In this case a steady decrease occurs down to 57% after eight weeks, this value being almost reached after just four weeks (61%).

5. Subsiding Pimples

The number of these efflorescences increased after only two weeks to 166%, after four weeks the initial value doubles (201%), and then slowly decreases again down to 141% after eight weeks.

6. Erythema Patches

After four weeks, the number of patches attains its highest value (146%), and at the end of the test is only slightly less (134%).

7. Degree of Inflammation (grades 1–4)

This rather general assessment makes clear the following:

The tester has the impression that the degree of inflammation declines almost linearly so that after just six weeks the optimum is attained (56%). Even after four weeks of the treatment period, this value at 65% is well below any possible placebo effect.

8. Subjective Assessment

The subjective data on the basis of the scale −10 to +10 reflect satisfactory acceptance by the patients. It is conspicuous that even at the first checkup (2 W) a value of +3.42 is achieved, which is only negligibly less than the six-week value of 3.46. At the end of the test there is obtained a mean value of +5.00; this means that the patients judge their skin condition to have improved to such an extent that they are half way to complete healing of their acne (+10).

9. Side Effects

Two patients out of 23 interrupted the test, on their own initiative, after five weeks, since they considered that the preparation caused to much irritation (reddening, itching, scaling).

The remaining patients indicated almost without exception a slight burning and reddening of the facial skin during and shortly after application, but this disappeared again very rapidly and was willingly tolerated by nearly all patients.

Summay and Assessment

For evaluation purposes there were available efflorescence counts from 20 acne patients who had applied the new acne preparation twice daily for eight weeks.

It is evident that the open comedones (40%) and inflamed efflorescences (active pimples and pustules) undergo the greatest reduction (57% and 22%, respectively, after eight weeks). The steep decrease of these efflorescence counts is very noticeable; said counts even after two weeks, are well below those which could be attributed to a placebo effect.

Conversely, the similarly steep increase in subsiding erythema patches and pimples fits in with this development, both of which serve as an indication of healing. These phenomena together may be interpreted as a rapidly commencing activity in the dynamics of the acne in the direction of an improvement.

After six weeks of treatment there occurs a substantially greater reduction in open comedones and in both lesions which represent the healing stages of inflammation.

Accordingly, the success of the treatment may be designated as being drastic and rapid. This is also revealed by the degree of inflammation, which, even after six weeks, is reduced almost by half and has the same value after eight weeks.

Compared with other acne preparations, e.g., benzoyl peroxide, which in previous tests were subjected to investigation regarding their effectiveness in the same methodology, the new acne preparation offers the prospect of greater activity in respect to the commencement of action and intensity of effect.

This is confirmed by the subject impression of the tester who considers the solution to be of equal value to the present favorite in acne therapy, i.e., vitamin A acids and benzoyl peroxide, and even to be superior with regard to skin irritation.

Similarly, the quality of the preparation is confirmed by the subjective assessment made by the patients (+5.00), which in previous tests had never exceeded a value higher than +3.50.

It should be pointed out that, without pyridine-3-aldehyde, none of the other constituents of the acne solution according to Example 11 showed any significant effect, either alone or together.

It is claimed:

1. A process for the topical treatment of acne vulgaris in humans which comprises applying to the lesions thereof a therapeutic composition comprising a pharmaceutically compatible topical carrier and an effective amount for treating said acne vulgaris of a pyridine aldehyde having the formula:

$$(CH_3)_n \text{—} \underset{N}{\underset{|}{\bigcirc}} \text{—} C \underset{O}{\overset{H}{\diagup}}$$

where n is 0 or 1, the aldehyde group being in the 2-, 3- or 4-position, and the methyl group being in the 2- or 6-position.

2. A process as recited in claim 1 in which the pyridine aldehyde is pyridine-3-aldehyde.

3. A process as recited in claim 1 in which the effective amount of the pyridine aldehyde is from approximately 0.05 to 5% by weight.

4. A process as recited in claim 1 in which the therapeutic composition also contains approximately 5 to 40% by weight of lactic acid ethyl ester.

5. A process as recited in claim 2 in which the effective amount of the pyridine-3-aldehyde is approximately 0.05 to 5% by weight.

6. A process as recited in claim 2 in which the therapeutic composition also contains approximately 5 to 40% by weight of lactic acid ethyl ester.

* * * * *